(12) United States Patent
Kintzig et al.

(10) Patent No.: US 7,643,997 B2
(45) Date of Patent: Jan. 5, 2010

(54) HANDHELD ANALYSIS INSTRUMENT HAVING ACOUSTIC OUTPUT OF MEASUREMENT RESULTS

(75) Inventors: Hans Kintzig, Tiefenthal (DE); Jean Thilges, Walldorf (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 642 days.

(21) Appl. No.: 11/422,175

(22) Filed: Jun. 5, 2006

(65) Prior Publication Data

US 2006/0277048 A1 Dec. 7, 2006

(30) Foreign Application Priority Data

Jun. 4, 2005 (EP) .................................. 05012092

(51) Int. Cl.
*G10L 21/06* (2006.01)
(52) U.S. Cl. ..................................................... 704/271
(58) Field of Classification Search .................. 704/271
See application file for complete search history.

(56) References Cited

U.S. PATENT DOCUMENTS 6,440,068 B1 * 8/2002 Brown et al. ................. 600/300

FOREIGN PATENT DOCUMENTS

| DE | 43 34 273 A1 | 4/1995 |
| DE | 199 02 972 A1 | 8/2000 |
| EP | 1 172 651 A1 | 1/2002 |
| JP | 09094231 | 4/1997 |
| WO | WO 03/017832 A2 | 3/2003 |
| WO | WO 03/017832 A3 | 3/2003 |

* cited by examiner

*Primary Examiner*—Susan McFadden
(74) *Attorney, Agent, or Firm*—Justin L. Sage; Roche Diagnostics Operations, Inc.

(57) ABSTRACT

The present invention relates to a handheld analysis instrument for assaying a medically significant sample. The instrument comprises a measuring device for measuring the concentration of an analyte in the sample, an output device for outputting measurement results. The output device has both an acoustic signal output device for outputting the measurement results through nonverbal acoustic signals and also a wireless interface for communicating with an external speech output unit.

16 Claims, 2 Drawing Sheets

HANDHELD ANALYSIS INSTRUMENT HAVING ACOUSTIC OUTPUT OF MEASUREMENT RESULTS

REFERENCE TO RELATED APPLICATIONS

The present application is based on European Patent Application No. 05012092.2, filed Jun. 4, 2005, which is hereby incorporated by reference in its entirety.

TECHNICAL FIELD

The present invention relates to a handheld analysis instrument for assaying a medically significant sample, in particular for determining the glucose concentration in a body liquid.

BACKGROUND

A typical handheld analysis instrument is known to have a display, which may be plugged into an external speech output unit so that contacts are closed and measurement results may be outputted verbally via the speech output unit. The known analysis system having an external speech output unit makes things much easier for visually impaired users who are able to recognize measurement results displayed on a display only with great difficulty or not at all.

However, the known analysis system have the disadvantage that the external speech output unit is relatively large, expensive, and cumbersome. Diabetics must measure their blood sugar level multiple times daily. Therefore, it is troublesome for them to carry along the external speech output unit. The user comfort of the known system is thus restricted.

SUMMARY

An object of the present invention is thus to indicate a way in which the user comfort of an analysis system allowing acoustic output of measurement results may be increased for visually-impaired diabetics.

This object is achieved according to the present invention by a handheld analysis instrument for assaying a medically significant sample, in particular for determining the glucose concentration of diabetics. The instrument has a measurement device for measuring the concentration of an analyte in the sample. An output device for outputting measurement results, which are determined by the measurement device. The output device has both an acoustic signal output device for outputting the measurement results through nonverbal acoustic signals and also a wireless interface for communication with an external speech output unit, by which the measurement results may be outputted verbally. The output device has an acoustic mode, in which measurement results may be outputted using the acoustic signal output device, and a speech output mode, in which measurement results may be outputted via the interface. The transition of the output device from the acoustic mode to the speech output mode being triggered by receiving a signal transmitted by the speech output unit.

The object is also achieved by an analysis system comprising such a handheld analysis instrument and a speech output unit, which has a wireless interface for communication with the handheld analysis instrument.

The combination of an acoustic signal output device for outputting the measurement results by nonverbal acoustic signals with a wireless interface for communication with an external speech output unit, provides the user with the comfort of a speech output in the majority of measurements, without a speech output unit having to be carried along. If the user is at home during measurements, a speech output may occur via the wireless interface by the speech output unit. For situations in which the user performs measurements outside his home, an acoustic signal output device integrated into the handheld analysis instrument is available, for outputting the measurement results through nonverbal acoustic signals. Thus, even for a blind user, it is not necessary to continuously carry along the speech output unit.

Measurement results and other information may be outputted by the acoustic signal output device through systems of Morse-like beeps or beeps of various frequencies, which are easy to understand and learn independently of speech and culture group, for example.

The wireless interface of a handheld analysis instrument according to the present invention contains a transmitter and a receiver. In a corresponding way, the interface of the external speech output unit also contains a transmitter and a receiver. The transmitter and the receiver of the handheld analysis instrument and the transmitter and the receiver of the external speech output unit are preferably each combined into a transceiver unit.

A further advantage of the present invention is that visually-impaired users may use the speech output unit for multiple generations of handheld analysis instruments. The use of a standardized communication protocol and a wireless interface which remains essentially uniform allows the compatibility of different handheld analysis instruments with the same speech output unit. By separating analysis instrument and speech output unit, the special requirements of visually-impaired users may be addressed ideally and a comfortable and cost-effective analysis system may be provided using the cost advantages of mass production.

The present invention will be explained in more detail hereafter on the basis of an exemplary embodiment illustrated in the attached figures. The special features illustrated therein may be used individually or in combination to provide preferred embodiments.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood reference is made to the following examples, which are intended to illustrate the invention, but not limit the scope thereof.

DETAILED DESCRIPTION

The following description of the preferred embodiment is merely exemplary in nature and is in no way intended to limit the invention or its application or uses.

Figure 1:
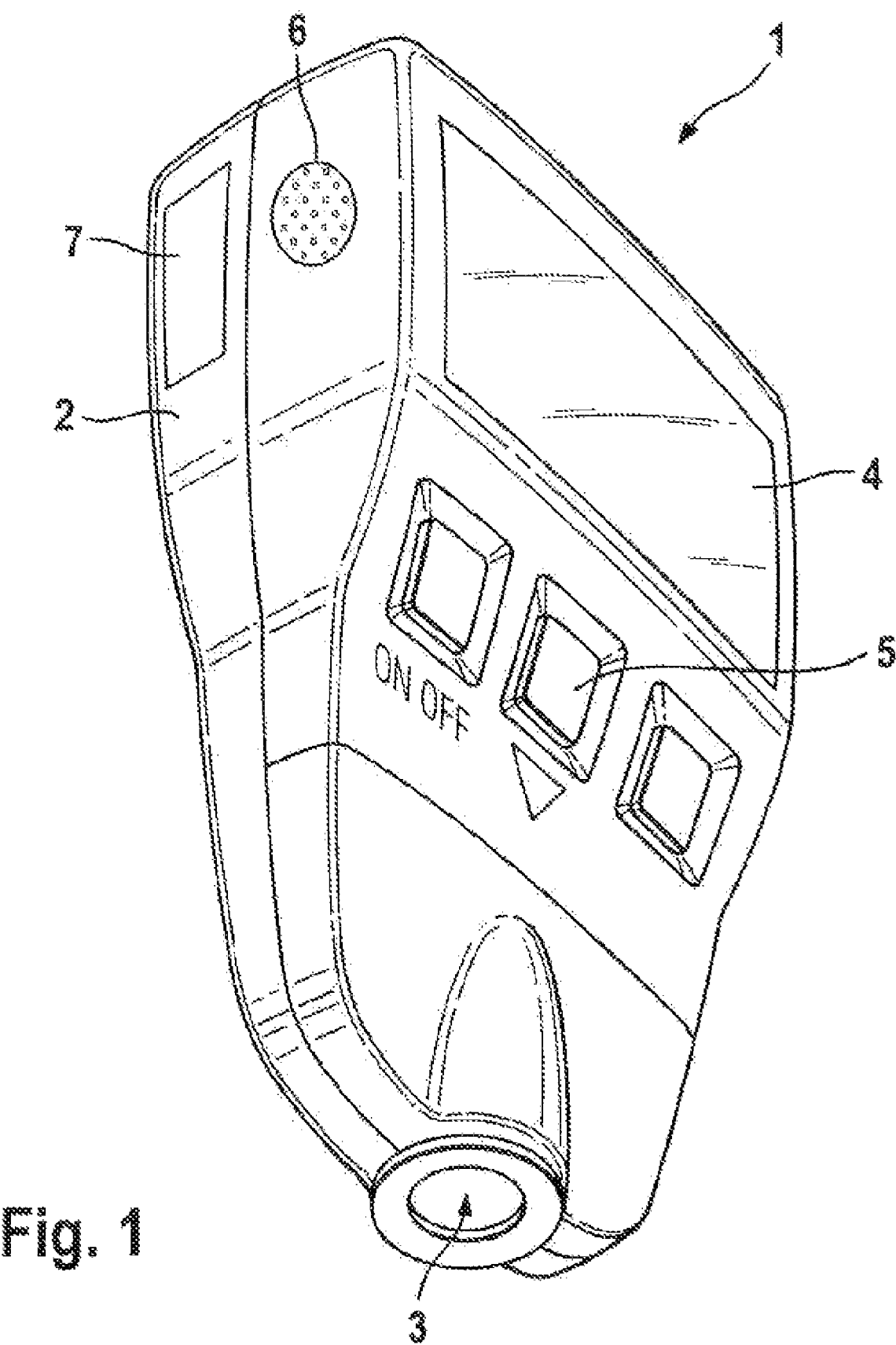
FIG. 1 shows an exemplary embodiment of a handheld analysis instrument according to the present invention.

The handheld analysis instrument 1 shown in FIG. 1 is a device for measuring the blood glucose content for diabetics. A lancet (not shown), for producing a puncture wound in a body part such as finger, is located in the device. Alternatively, a separate lancing device such as those commercially sold under the name Accu-Chek SOFTCLIX lancing device may also be used to puncture a body part.

The body part may be applied to an opening 3 of the housing 2. The device 1 automatically absorbs blood coming out of the puncture wound and determines a blood glucose concentration value using an internal measuring device (not shown). Operating elements 5 in the form of buttons are provided for actuating the device 1 and/or for using special functions.

The handheld analysis instrument 1 has an output device for outputting measurement results, which have been determined using the measuring device. Measuring device and output device are connected to a mains-independent power source, such as batteries or solar cells. The output device comprises both an acoustic signal output device 6 for outputting the measurement results by nonverbal acoustic signals, such as beeps, and also a wireless interface 7 for communicating with an external speech output unit (FIG. 2), suitable to output verbally the measurement results.

The wireless interface 7 may be an infrared interface, in which an infrared transmitter and an infrared receiver are integrated, so that data may be exchanged with the external speech output unit through infrared radiation. Instead of an infrared interface having an infrared transmitter and an infrared receiver, data transmission by radio or through ultrasound may also be used for communication between the handheld analysis instrument 1 and the external speech output unit 10 (shown in FIG. 2). Alternatively, Bluetooth communication or such standard communication technology may also be use for wireless connection between the wireless interface 7 and the external speech output unit 10.

The output device has an acoustic mode, in which measurement results are outputted by means of the acoustic signal output device 6, and a speech output mode, in which measurement results are outputted by the wireless interface 7 and the external speech output unit. A transition of the output device from the acoustic mode to the speech output mode is triggered by receiving a "ready-to-operate" signal transmitted by the speech output unit.

The output device of the handheld analysis instrument 1 illustrated in FIG. 1 additionally comprises an optical indication device 4 in form of a display. The output device may be switched by an operating element 5 which may be actuated by the user, between the acoustic mode, in which measurement results are outputted by the acoustic signal output device 6, and a visual mode, in which measurement results are outputted by the optical indication device 4. The measurement results are additionally displayed by the indication device 4 in the acoustic mode. Measurement results may also additionally displayed by the indication device 4 in the speech output mode.

The acoustic signal output device 6, the external speech output unit, and the optical indication device 4 may be used not only to output measurement results, but also to output operating information. For example, such information may include information about the status of the device 1. The operating information is also outputted in the speech output mode by the acoustic signal output device and the indication device 4. For example, a device status may be indicated by a beep sequence, such as results of self tests of the handheld analysis instrument or the charge status of the batteries. An important device status as defined here also relates to the question of whether the device 1 is ready for a puncture and a subsequent glucose concentration measurement or whether a sample has been taken correctly from a finger positioned at the opening 3. Outputting operating information of this type via the acoustic signal output device 6 is in particular also advantageous. When handling the device 1, the infrared interface 7 may temporarily be covered or interfered with by sunlight, so that data exchange with the external speech output unit is no longer possible.

Figure 2:
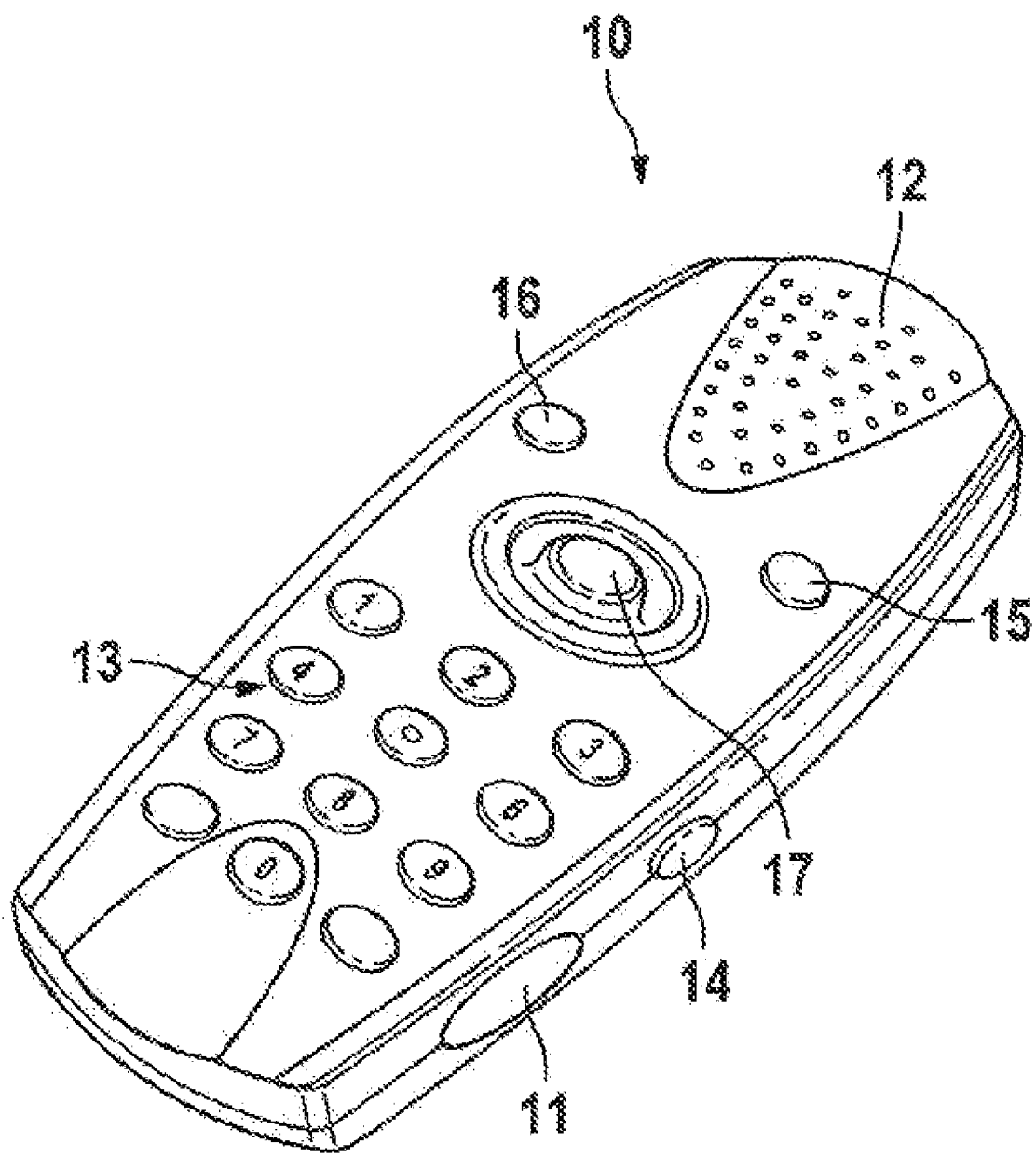
FIG. 2 shows an exemplary embodiment of an external speech output unit for the handheld analysis instrument shown in FIG. 1.

The external speech output unit 10 for the handheld analysis instrument 1 described with regard to FIG. 1 is illustrated in FIG. 2. The speech output unit 10 has a wireless interface 11 for communication with the handheld analysis instrument 1 via its wireless interface 7. The interface 11 of the speech output unit 10 is implemented for bidirectional information exchange like the interface 7 of the handheld analysis instrument 1. In the case of infrared interfaces, the two interfaces 7 and 11 therefore have an infrared transmitter and an infrared receiver. The external speech output unit 10 has the same communication protocol as the wireless interface 7 of the handheld instrument 1.

Measurement results and/or operating information may be outputted by the speech output unit 10 verbally via a loudspeaker 12. The speech output unit 10 also has operating elements in the form of a keyboard 13, a laterally attached button 14 for regulating the volume, additional operating buttons 15, 16, and a steering control 17 similar to a joystick.

The steering control 17 has a construction and function corresponding to steering controls typical for laptops, for moving a cursor on a display screen, for example, to select points from a context menu. In the illustrated speech output unit 10, a display screen of this type is not provided since it would not be usable for blind users. A blind user may nevertheless select entry from a virtual table by the steering control 17. These entries may for example, be subpoints of a function menu or historic measurement data being stored in a measured value table.

The storage of measured data is of great significance for visually-impaired users since, these people may record medical data in a diary for a treating physician not at all or only with great difficulty. A diary function is thus made possible for users by a memory (not shown) of the external analysis unit 10. This diary function is supported by input devices such as the numeric keyboard 13 and the steering control 17.

While the handheld analysis instrument 1 has a mains-independent power source, such as batteries, the speech output unit 10 may be provided with a power cable for connection to the general power mains. However, the speech output unit 10 is preferably also provided with a mains-independent power sources, preferably batteries.

The handheld analysis instrument 1 and the external speech output unit 10 form an analysis system which offers high user comfort for visually-impaired people. The speech output unit 10 transmits ready-to-operate signals at predefined time intervals of approximately half a minute. If the handheld analysis instrument 1 receives such an ready-to-operate signal, it answers with an identification signal and exchanges a series of synchronization pulses with the speech output unit 10 according to a communication protocol. Synchronization of date and time of day is also being performed. During the communication, the speech output unit 10 takes over a master function and queries operational and device data of the handheld analysis instrument 1. For example, in this way, the device type and serial number of the handheld analysis instrument 1, the device status, and its memory contents are communicated to the speech output unit 10. After the handheld analysis instrument 1 and the speech output unit 10 have communicated via the communication protocol, the output device of the handheld analysis instrument 1 changes from the acoustic mode into the speech output mode and transmits the measurement results to be outputted. By pressing the repeat button 15 of the speech output unit 10, a repetition of an acoustical output of measurement results may be caused.

Establishing communications between the handheld analysis instrument 1 and the external speech output unit 10 may be initiated in principle by either of the two devices. Therefore, it is also possible that the handheld analysis instrument 1 transmits a search signal each time it is turned on and that the speech output unit 10 replies thereto. For both cases of establishing communication, it is preferable that the speech output unit 10 takes over a master function and queries operational and device data from handheld analysis instrument 1. In this case, the speech output unit 10 compares an identification signal transmitted by the handheld analysis instrument 1 to a stored identification signal. If this comparison does not show correspondence, the communication is terminated. So only measured data of the user is outputted and stored by the speech output unit. For rapidly establishing communication, it is favorable if the interface 7 of the handheld analysis instrument 1 is adapted to transmit and receive simultaneously. This may be achieved by an appropriate control device, in the form of a suitably programmed microprocessor, for example. It is also possible for both the handheld analysis instrument 1 and the external speech output unit 10 to be switched to receive periodically after transmitting data. In this case different time periods are preferably used for the handheld analysis instrument 1 and the speech output unit 10.

If the communication between the handheld analysis instrument 1 and the external speech output unit 10 is interrupted or establishing communication between the two devices 1, 10 using the predefined communication protocol fails, the handheld analysis instrument 1 automatically switches into the acoustic mode. During the communication, the output device and the speech output unit 10 regularly exchange confirmation signals using the communication protocol. If a confirmation signal of the speech output unit 10 fails, the output device switches automatically into the acoustic mode.

An important advantage of the external speech output unit 10 is that a user may not only have measurement results communicated verbally, but also status and operating information of the handheld analysis instrument 1 may be provided in detailed and comprehensive form. The speech output unit 10 has a memory (not shown) for this purpose, in which the user manual of the analysis system is stored partially or completely, preferably in the form of MP3 files, so that its content may be made verbally accessible to a user.

By pressing the help button 16, a help function is activated and a verbal output is caused outputting the relevant parts of the user manual for the currently existing operational or operating status of the analysis system. If the help button 16 is actuated again during a verbal output of health information, the output is interrupted and only continued after the button 16 is actuated once again. In this way, the user has the ability to adapt the speed of the information flow to his receptiveness.

In the analysis system described, a user may select between three different types of operation of the acoustic signal output device 6 by the operating elements 5. The first type of operation is the described acoustic mode in which both measurement results and also status information of the device 1 are outputted by beeps. The second type of operation is a restricted acoustic mode in which only status information is outputted by beeps. Measurement results are only outputted via the speech output unit 10 and/or the optical indication device 4. In a third type of operation, the acoustic signal output device 6 may be turned off entirely (visual mode, mute switch), so that neither measurement results nor status information are outputted by beeps. In the latter types of operations the handheld analysis instrument 1 may also be used by people having normal vision, who may possibly feel disturbed by beeps. In this way, the handheld analysis instrument 1 may be produced in larger numbers, so that cost advantages result through corresponding mass production.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically although some aspects of the present invention are identified herein as preferred or particularly advantageous, it is contemplated that the present invention is not necessarily limited to these preferred aspects of the invention.

What is claimed is:

1. A handheld analysis instrument for assaying a medically significant sample, the handheld analysis instrument comprising:
  a measuring device for measuring the concentration of an analyte in the sample; and
  an output device for outputting measurement results which were determined by the measuring device, the output device being configured to operate in one or the other of an acoustic mode for outputting the measurement results through nonverbal acoustic signals and a speech output mode for outputting the measurement results verbally, wherein the output device comprises:
  an acoustic signal output device for operation in the acoustic mode; and
  a wireless interface comprising a transmitter and a receiver for wirelessly communicating with a wireless interface of a speech output unit external to the analysis instrument, by which the measurement results are outputted verbally via the interface of the output device when operating in the speech output mode;
  and wherein a transition of the output device from the acoustic mode into the speech output mode is triggered by reception of a signal transmitted by the speech output unit via the wireless interface of the output device and of the external speech output unit.

2. The handheld analysis instrument according to claim 1, wherein the acoustic signal output device generates beeps to output the measurement results.

3. The handheld analysis instrument according to claim 1, wherein the output device returns automatically from the speech output mode into the acoustic mode if it no longer receives the signal from the speech output unit.

4. The handheld analysis instrument according to claim 1, wherein the output device further comprises an optical indication device.

5. The handheld analysis instrument according to claim 4, further comprising an operating element, which may be actuated by the user and by which the output device may be switched over between an acoustic mode, in which measurement results are outputted using the acoustic signal output device, and a visual mode, in which measurement results are outputted using the optical indication device.

6. The handheld analysis instrument according to claim 4, wherein in the acoustic mode measurement results are additionally displayed using the optical indication device.

7. The handheld analysis instrument according to claim 1, wherein the interface is an infrared interface.

8. The handheld analysis instrument according to claim 1, wherein in the speech output mode, operating information is outputted via the acoustic signal output device and/or the indication device.

9. An analysis system for analyzing a medically significant analyte, the system comprising:
    a handheld analysis instrument comprising a measuring device for measuring the concentration of an analyte in the sample and an output device for outputting measurement results which were determined by the measuring device, the output device being configured to operate in one or the other of an acoustic mode for outputting the measurement results through nonverbal acoustic signals and a speech output mode for outputting the measurement results verbally; and
    a speech output unit external to the analysis instrument and having a wireless interface adapted for communicating with the handheld analysis instrument,
    wherein the output device transitions from the acoustic mode for nonverbally outputting measurement results to the speech output mode for verbally outputting measurement results when the speech output unit communicates with the handheld instrument via the wireless interface.

10. The system according to claim 9, wherein the output device comprises:
    an acoustic signal output device for operation in the acoustic mode for nonverbally outputting the measurement results; and
    an interface for communicating with the external speech output unit, such that the output device operates in the speech output mode for verbally outputting the measurement results;
    wherein the output device transitions from the acoustic mode into the speech output mode upon receiving a signal transmitted by the speech output unit.

11. The system according to claim 10, wherein the wireless interface of the speech output unit and the interface of the output device communicate with each other wirelessly.

12. The system according to claim 10, wherein the acoustic signal output device generates beeps to output the measurement results.

13. The system according to claim 10, wherein the output device returns automatically from the speech output mode into the acoustic mode if it no longer receives the signal from the speech output unit.

14. The system according to claim 9, wherein the output device further comprises an optical indication device.

15. The system according to claim 14, further comprising an operating element, which may be actuated by the user and by which the output device may be switched over between an acoustic mode, in which measurement results are outputted using the acoustic signal output device, and a visual mode, in which measurement results are outputted using the optical indication device.

16. The system according to claim 14, wherein in the acoustic mode measurement results are additionally displayed using the optical indication device.

* * * * *

UNITED STATES PATENT AND TRADEMARK OFFICE
CERTIFICATE OF CORRECTION

| | |
|---|---|
| PATENT NO. | : 7,643,997 B2 |
| APPLICATION NO. | : 11/422175 |
| DATED | : January 5, 2010 |
| INVENTOR(S) | : Kintzig et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 856 days.

Signed and Sealed this

Sixteenth Day of November, 2010

David J. Kappos
*Director of the United States Patent and Trademark Office*